(12) United States Patent
Kraemer et al.

(10) Patent No.: US 9,161,754 B2
(45) Date of Patent: Oct. 20, 2015

(54) APPARATUS AND METHOD FOR CONCURRENTLY FORMING A GASTROESOPHAGEAL VALVE AND TIGHTENING THE LOWER ESOPHAGEAL SPHINCTER

(71) Applicant: EndoGastric Solutions, Inc., Redmond, WA (US)

(72) Inventors: Stefan J. M. Kraemer, Seattle, WA (US); Brett J. Carter, Monroe, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 196 days.

(21) Appl. No.: 13/716,061

(22) Filed: Dec. 14, 2012

(65) Prior Publication Data

US 2014/0171969 A1  Jun. 19, 2014

(51) Int. Cl.
*A61B 17/08* (2006.01)
*A61B 17/04* (2006.01)
*A61B 17/02* (2006.01)
*A61B 17/29* (2006.01)
*A61B 17/00* (2006.01)
*A61B 17/30* (2006.01)

(52) U.S. Cl.
CPC .............. *A61B 17/08* (2013.01); *A61B 17/0401* (2013.01); *A61B 17/0218* (2013.01); *A61B 17/29* (2013.01); *A61B 2017/003* (2013.01); *A61B 2017/00349* (2013.01); *A61B 2017/00827* (2013.01); *A61B 2017/0409* (2013.01); *A61B 2017/0419* (2013.01); *A61B 2017/306* (2013.01)

(58) Field of Classification Search
CPC .. A61B 17/0401; A61B 17/08; A61B 17/218; A61B 17/29; A61B 17/0218
USPC ......... 606/151, 142, 157, 219, 228, 232, 139, 606/153, 213, 215; 607/133; 623/23.64, 623/23.68
See application file for complete search history.

(56) References Cited

U.S. PATENT DOCUMENTS

2007/0112363 A1* 5/2007 Adams .......................... 606/153
2007/0129738 A1* 6/2007 Kraemer et al. .............. 606/153

* cited by examiner

*Primary Examiner* — Jocelin Tanner
(74) *Attorney, Agent, or Firm* — Fulwider Patton LLP

(57) ABSTRACT

An apparatus enables concurrent restoration of a gastroesophageal valve and tightening of the lower esophageal sphincter. The apparatus comprises a longitudinal member having a distal end arranged to be received within a stomach, a tissue shaper at the distal end of the longitudinal member that forms a gastroesophageal valve from stomach tissue, and a tissue gatherer that gathers fundus tissue at or aboral to the gastroesophageal junction to reduce an esophageal opening into the stomach and tighten the lower esophageal sphincter. A fastener deployer then deploys at least one fastener pair to maintain both the restored gastroesophageal valve and the tightened lower esophageal sphincter.

8 Claims, 7 Drawing Sheets

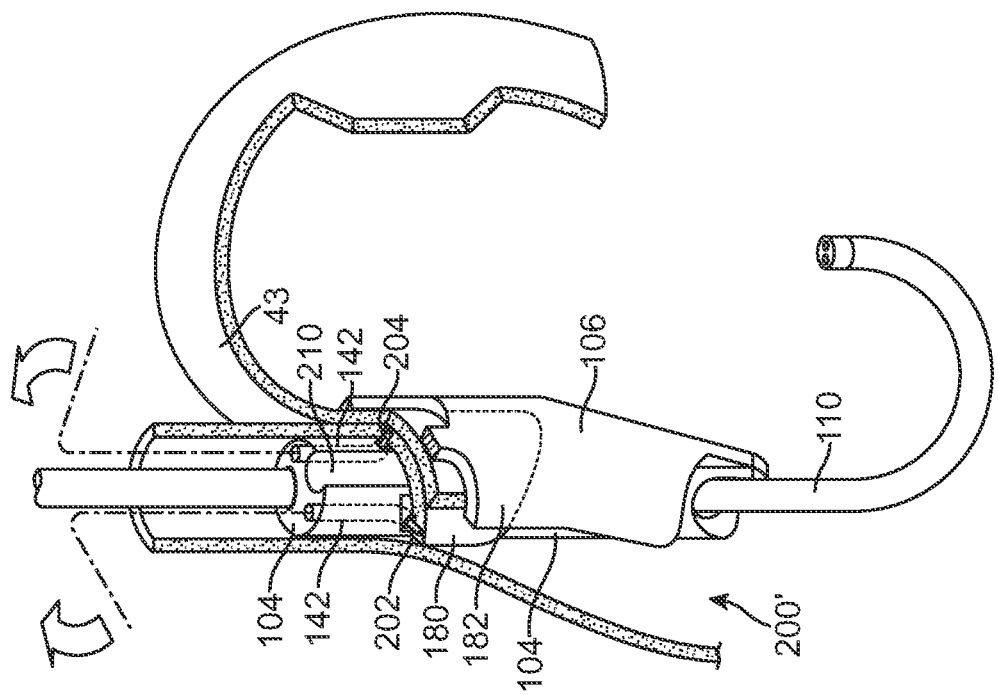
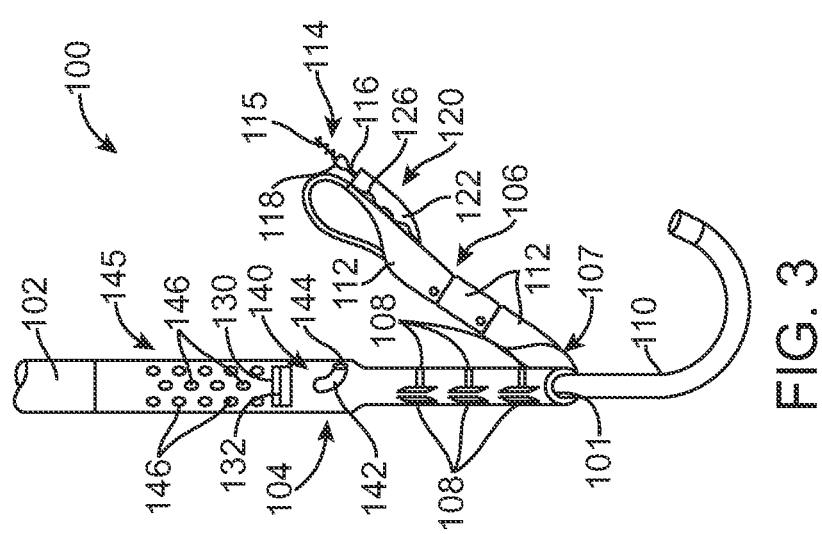

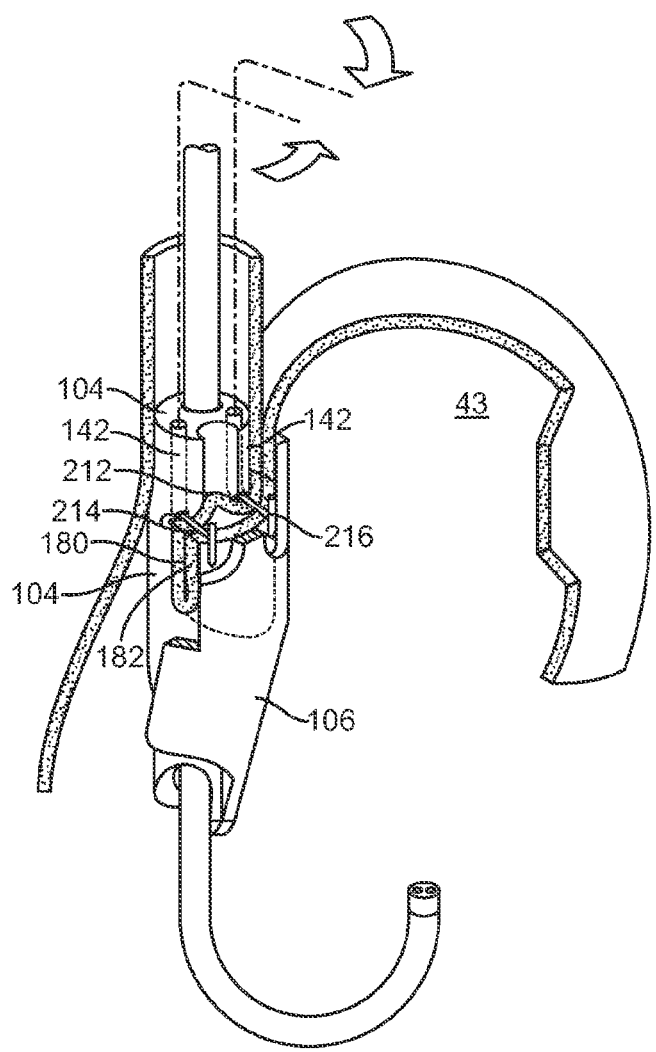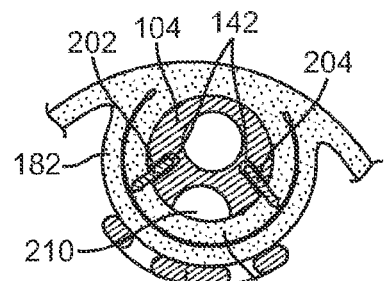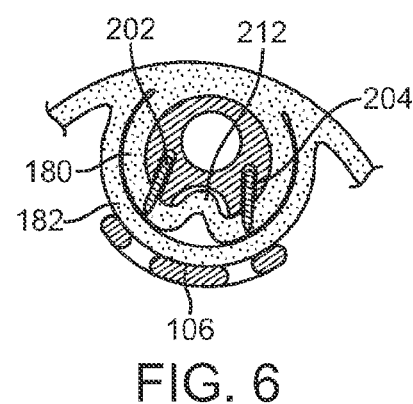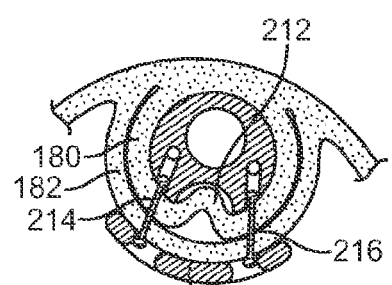

APPARATUS AND METHOD FOR CONCURRENTLY FORMING A GASTROESOPHAGEAL VALVE AND TIGHTENING THE LOWER ESOPHAGEAL SPHINCTER

This application is a continuation of U.S. application Ser. No. 12/870,815 filed Aug. 28, 2010, which is a continuation of U.S. application Ser. No. 12/319,228 filed Jan. 2, 2009 (now abandoned), which is a continuation of U.S. application Ser. No. 11/291,500 filed Dec. 1, 2005 (now abandoned). The entire disclosures of which are herein incorporated by reference.

FIELD OF THE INVENTION

The present invention generally relates to manipulation of stomach tissue as by folding or molding and stomach tissue fixation to treat gastroesophageal reflux disease. The present invention more particularly relates to the restoration of a gastroesophageal valve and the concurrent tightening of the lower esophageal sphincter.

BACKGROUND

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat, and will digest esophageal tissue when persistently splashed into the esophagus.

A principal reason for regurgitation associated with GERD is the mechanical failure of a deteriorated gastroesophageal valve to close and seal against pressure in the stomach. Due to reasons including lifestyle, a Grade I normal gastroesophageal valve may deteriorate into a malfunctioning Grade III or absent gastroesophageal valve Grade IV. With a deteriorated gastroesophageal valve, the stomach contents are more likely to be regurgitated into the esophagus, the mouth, and even the lungs. The regurgitation is referred to as "heartburn" because the most common symptom is a burning discomfort in the chest under the breastbone. Burning discomfort in the chest and regurgitation of sour-tasting gastric juice into the mouth are classic symptoms of gastroesophageal reflux disease (GERD). When stomach acid is regurgitated into the esophagus, it is usually cleared quickly by esophageal contractions and esophageal clearance as a result from swallowing. Heartburn as a result from backwashing of stomach acid and bile onto the esophagus results when stomach acid is frequently regurgitated into the esophagus and the esophageal wall is inflamed.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by a precancerous lining called Barrett's Esophagus in which a cancerous esophageal adenocarcinoma can develop.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is in a supine position and sleeping. Occasionally, a person with severe GERD will be awakened from sleep with a choking sensation. Hoarseness can also occur due to acid reaching the vocal cords, causing a chronic inflammation or injury.

GERD never improves without intervention. Life style changes combined with both medical and surgical treatments exist for GERD. Medical therapies include antacids; anti-secretory drugs such as H2-blockers, and proton pump inhibitors. However, the medical therapies only mask the reflux. Patients still get reflux, asthma, and perhaps even emphysema because of gastric contents and particles refluxed into the lungs. Barrett's esophagus results in about 10% of the GERD cases. The esophageal epithelium changes into intestinal metaplastic epithelium tissue that tends to become cancerous from repeated acid washing despite the medication.

Several open laparotomy and laparoscopic surgical procedures are available for treating GERD. One surgical approach is the Nissen fundoplication. The Nissen approach typically involves a 360-degree wrap of the fundus around the gastroesophageal junction. The procedure has a high incidence of postoperative complications. The Nissen approach creates a 360-degree moveable valve, typically without a fixed portion. Hence, Nissen does not restore the normal movable flap of the valve. The patient's frequency cannot burp because the fundus was used to make the repair by wrapping it around the esophagus, and may experience dysphagia. Another surgical approach to treating GERD is the Belsey Mark IV (Belsey) fundoplication. The Belsey procedure involves creating a valve by suturing a portion of the stomach to an anterior surface of the esophagus. It reduces some of the postoperative complications encountered with the Nissen fundoplication, but still does not restore an anatomical normal movable flap. None of these procedures fully restores the normal anatomical anatomy or produces a normally functioning gastroesophageal junction. Another surgical approach is the Hill repair. In the Hill repair, the gastroesophageal junction is anchored to the posterior abdominal areas, and a 180-270 degree valve is created by a system of sutures. The Hill procedure restores the moveable flap, the cardiac notch and the Angle of His. However, all of these surgical procedures are very invasive, regardless of whether done as a laparoscopic or an open procedure.

New, less surgically invasive approaches to treating GERD involve transoral endoscopic procedures. One procedure contemplates a machine device with robotic arms that is inserted transorally into the stomach. While observing through an endoscope, an endoscopist guides the machine within the stomach to engage a portion of the fundus with a corkscrew-like device on one arm. The arm then pulls on the engaged portion to create a fold of tissue or radial plication at the gastroesophageal junction. Another arm of the machine pinches the excess tissue together and fastens the excess tissue with one pre-tied implant. This procedure does not restore normal anatomy. The fold created does not have anything in common with a valve. In fact, the direction of the radial fold prevents the fold or plication from acting as a flap of a valve.

Another transoral procedure contemplates making a fold of fundus tissue near the deteriorated gastroesophageal flap to recreate the lower esophageal sphincter (LES). The procedure requires placing multiple U-shaped tissue clips around the folded fundus to hold it in shape and in place.

This and the previously discussed procedure are both highly dependent on the skill, experience, aggressiveness, and courage of the endoscopist. In addition, these and other procedures may involve esophageal tissue in the repair. Esophageal tissue is fragile and weak, in part due to the fact, that the esophagus is not covered by serosa, a layer of very sturdy, yet very thin tissue, covering and stabilizing all intraabdominal organs, similar like a fascia covering and stabilizing muscle. Involvement of esophageal tissue in the repair of a gastroesophageal valve poses unnecessary risks to the patient, such as an increased risk of fistulas between the esophagus and the stomach and the risk of mediastinitis.

A new and improved apparatus and method for restoration of a gastroesophageal valve is fully disclosed in U.S. Pat. No. 6,790,214, issued Sep. 14, 2004, is assigned to the assignee of this invention, and is incorporated herein by reference. That apparatus and method provides a transoral endoscopic gastroesophageal valve restoration. A longitudinal member arranged for transoral placement into a stomach carries a tissue shaper that non-invasively grips and shapes stomach tissue. A tissue fixation device is then deployed to maintain the shaped stomach tissue in a shape approximating a gastroesophageal flap.

The last mentioned apparatus and method hold out great promise for the GERD sufferer. Not only are the gastroesophageal valve anatomy and function restored, they are restored transorally without the need for surgical incisions. Most patients will experience a quick recovery to a better life without GERD in a few days. Most won't even need to spend a night in the hospital.

Experience has shown that a significant percentage of patients who suffer from GERD also have a compromised high-pressure zone and lower esophageal sphincter (LES). The compromised function of the LES is exhibited by enlargement of the perimeter of the LES and a weakened state of its associated muscle tissue. While a healthy lower esophageal sphincter serves as a discriminating sphincter, able to distinguish between burping gas, liquids, and solids, and supporting the valve to prevent reflux from happening, a compromised LES is unable to provide this function. Hence, a healthy LES provides an added protection against GERD when working in conjunction with the gastroesophageal valve (GEV), but a compromised LES does not.

Unfortunately, none of the prior art devices or methods address the issue of restoring both the LES and the GEV during a single (concurrent) procedure. Indeed, only the last mentioned apparatus and method are even directed to restoring the GEV. The others are solely intended to restore LES competency. Hence, there is a need in the art to address the total picture for treating GERD, restoring both the LES and the GEV to effective competency. The present invention addresses these and other issues.

SUMMARY

The invention provides a method of treating a gastrodisorder involving a patient's stomach, esophagus, and esophageal opening into the stomach. The method comprises forming a gastroesophageal valve from stomach tissue, gathering fundus tissue at or aboral of the gastroesophageal junction to reduce the esophageal opening, and deploying at least one fastener to maintain both the formed gastroesophageal valve and fundus fold.

The gathering step may comprise displacing the fundus tissue into the esophageal opening. The gathering step may comprise mechanically gripping the fundus tissue. The gathering step may alternatively comprise vacuum gathering the fundus tissue. The gathering step may include gathering the fundus tissue at a gathering point. The deploying step may comprise deploying a fastener on opposite sides of the gathering point.

The deploying step may comprise deploying at least a pair of fasteners spaced apart and the gathering step may comprise providing the fasteners with converging trajectories during deployment.

The method may further comprise the step of placing a medical instrument into the stomach, and the step of forming a gastroesophageal valve may comprise folding stomach tissue with the instrument so that serosa tissue contacts serosa tissue to form a flap of stomach tissue layers. The stomach tissue layers comprise an inner tissue layer and an outer tissue layer, and the gathering step may comprise gathering the inner tissue and displacing the inner tissue layer into the esophageal opening with the instrument. The gathering step may comprise mechanically gripping the inner tissue layer or vacuum gathering the inner tissue layer.

The gathering step may include gathering the inner tissue layer at a gathering point. The deploying step may include deploying a fastener with the instrument through the tissue layers on opposite sides of the gathering point.

The invention further provides a method of treating a stomach disorder involving a patient's stomach, esophagus, and esophageal opening into the stomach, comprising forming, in a plurality of stages, a gastroesophageal valve from stomach tissue, during at least one of the stages, gathering fundus tissue at or aboral of the gastroesophageal junction to reduce the esophageal opening and deploying at least one fastener to maintain both the formed gastroesophageal valve and reduced esophageal opening.

The gathering step may comprise gripping the fundus tissue and displacing the fundus tissue into the esophageal opening. The gathering step may again comprise mechanically gripping the fundus tissue or vacuum gathering the fundus tissue. Again, the gathering step may include gathering the fundus tissue at a gathering point and the deploying step may comprise deploying a fastener on opposite sides of the gathering point.

The deploying step may again comprise deploying at least a pair of fasteners spaced apart and the gathering step may comprise providing the fasteners with converging trajectories during deployment.

The method may further comprise the step of placing a medical instrument into the stomach, and the step of forming a gastroesophageal valve may comprise folding, during each stage, stomach tissue with the instrument so that serosa tissue contacts serosa tissue to form a flap of stomach tissue layers. The stomach tissue layers comprise an inner tissue layer and an outer tissue layer, and the gathering step may include gathering the inner tissue layer and displacing the inner tissue layer into the esophageal opening with the instrument. The instrument may gather the inner tissue layer at a gathering point and deploy a fastener on each side of the gathering point.

The instrument may be used to drive at least a pair of spaced apart fasteners from the inner tissue layer to and through the outer tissue layer and, while driving the fasteners, providing the fasteners with diverging drive trajectories to cause the tissue layers to be gathered.

The invention still further provides a method of restoring a patient's gastroesophageal valve associated with the patient's stomach, esophagus, and esophageal opening into the stomach, and concurrently, tightening the patient's lower esophageal sphincter. The method comprises forming, from stomach tissue, a plurality of gastroesophageal valve portions in a like plurality of serially repeated stages until the gastroesophageal valve is formed. During at least one of the stages, fundus tissue is gathered at or aboral of the gastroesophageal junction to form a fundus fold to reduce the esophageal opening. At least one fastener is then deployed to maintain both the gastroesophageal valve portion formed during the at least one stage and the fundus fold.

The invention further provides an apparatus arranged to treat a stomach disorder involving a patient's stomach, esophagus, and esophageal opening into the stomach. The apparatus comprises a longitudinal member having a distal end arranged to be received within a stomach, a tissue shaper at the distal end of the longitudinal member that forms a gastroesophageal valve from stomach tissue, a tissue gatherer that gathers fundus tissue at or aboral to the gastroesophageal junction to reduce the esophageal opening into the stomach, and a fastener deployer that deploys a fastener that maintains both the gastroesophageal valve and the reduced esophageal opening.

The gatherer may be arranged to displace the fundus tissue into the esophageal opening. The gatherer may comprise a mechanical gripper that grips the fundus tissue. The gatherer may alternatively comprise a vacuum gatherer that gathers the fundus tissue.

The gatherer may be arranged to gather the fundus tissue at a gathering point and the fastener deployer may be arranged to deploy a fastener on opposite sides of the gathering point.

The fastener deployer may be arranged to deploy at least a pair of fasteners spaced apart and the gatherer may be arranged to provide the fasteners with converging trajectories during deployment. The converging trajectories of the fasteners will cause gathering of the fundus tissue after fastener deployment.

The tissue shaper may comprise a tissue folder that folds stomach tissue such that serosa tissue contacts serosa tissue to form the gastroesophageal valve from stomach tissue layers.

The stomach tissue layers comprise an inner tissue layer and an outer tissue layer, and the gatherer may comprise a gatherer that gathers the inner tissue layer and displaces the inner tissue layer into the esophageal opening.

The gripper may arrange to mechanically grip the inner tissue layer. The gripper may alternatively be arranged to vacuum gather the inner tissue layer.

The gatherer may be arranged to gather the inner tissue layer at a gathering point and the fastener deployer may be arranged to deploy a fastener through the tissue layers on opposite sides of the gathering point.

The tissue shaper may comprise a pair of hingedly coupled first and second arms. The first and second arms are arranged to receive the tissue there between and to fold the stomach tissue to form the gastroesophageal valve.

Another apparatus for treating a stomach disorder involving a patient's stomach, esophagus, and esophageal opening into the stomach comprises a tissue shaper that forms, over a plurality of stages, a gastroesophageal valve from stomach tissue. The apparatus further comprises a tissue gatherer that folds fundus tissue at or aboral of the gastroesophageal junction during at least one of the stages to reduce the esophageal opening and a fastener deployer that deploys at least one fastener to maintain both the formed gastroesophageal valve and fundus fold.

According to a still further embodiment, an apparatus for restoring a patient's gastroesophageal valve associated with the patient's stomach, esophagus, and esophageal opening into the stomach, and concurrently, tightening the patient's lower esophageal sphincter comprises a tissue shaper that forms, from stomach tissue, a plurality of gastroesophageal valve portions in a like plurality of serially repeated stages until the gastroesophageal valve is formed. The apparatus further comprises a tissue gatherer that, during at least one of the stages, folds fundus tissue at or aboral of the gastroesophageal junction to form a fundus fold to reduce the esophageal opening and a fastener deployer that deploys at least one fastener to maintain both the gastroesophageal valve portion formed during the at least one stage and the fundus fold.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify like elements, and wherein:

FIG. 3 is a side view of an apparatus for restoring the flap of a GEV according to an embodiment of the invention;

FIG. 4 is a perspective view with portions cutaway of the apparatus of FIG. 3 according to an embodiment of the invention illustrating internal elements at an initial stage of concurrent tightening of the LES;

FIG. 5 is a sectional view illustrating a manner in which the device of FIGS. 3 and 4 may first grip fundus tissue for concurrently tightening the LES;

FIG. 6 is a sectional view showing the LES being concurrently tightened by the device of FIGS. 3 and 4;

FIG. 7 is a perspective view with portions cutaway of the apparatus of FIGS. 3 and 4 after deploying fasteners to maintain the concurrent tightening of the LES;

FIG. 8 is a sectional view showing the LES concurrently tightened by the device of FIGS. 3 and 4 after fasteners have been deployed;

DETAILED DESCRIPTION

Figure 1:
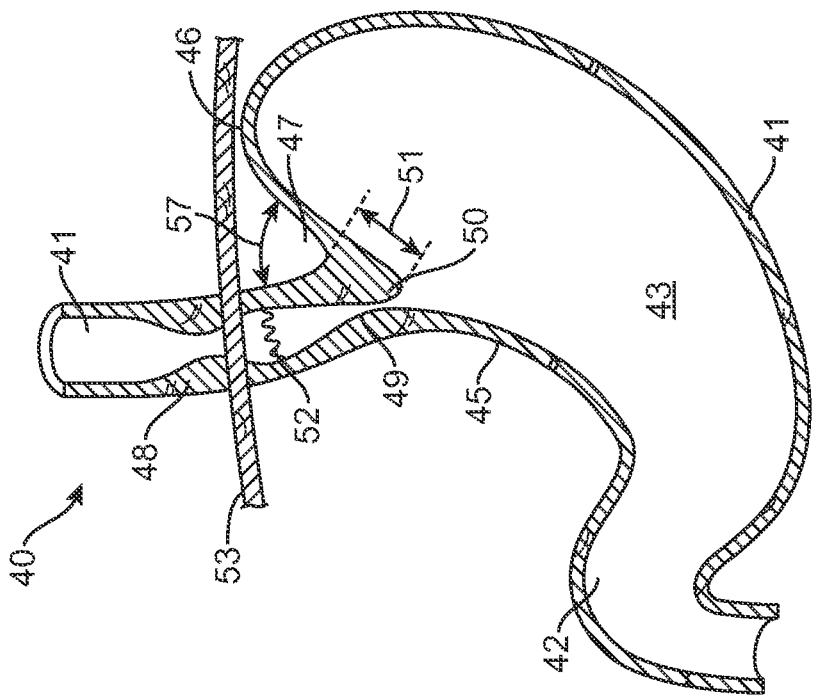
FIG. 1 is a front cross-sectional view of the esophageal-gastro-intestinal tract from a lower portion of the esophagus to the duodenum.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue.

The fundus 46 of the greater curvature 44 forms the superior portion of the stomach 43, and traps gas and air bubbles for burping. The esophageal tract 41 enters the stomach 43 at an esophageal orifice below the superior portion of the fundus 46, forming a cardiac notch 47 and an acute angle with respect to the fundus 46 known as the Angle of His 57. The lower esophageal sphincter (LES) 48 is a discriminating sphincter, which is part of the high-pressure zone of the antireflux barrier of the GEJ able to distinguish between burping gas, liquids, and solids, and works in conjunction with the fundus 46 to burp. The gastroesophageal valve (GEV) 49 includes a moveable portion and an opposing more stationary portion.

The moveable portion of the GEV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEV 49 comprises a portion of the lesser curvature 45 of the stomach 43 adjacent to its junction with the esophagus 41. The gastroesophageal flap 50 of the GEV 49 principally comprises tissue adjacent to the fundus 46 portion of the stomach 43. It is about 4 to 5 cm long (51) at it longest portion, and its length may taper at its anterior and posterior ends.

The gastroesophageal flap 50 is partially held against the lesser curvature 45 portion of the stomach 43 by the pressure differential between the stomach 43 and the thorax, and partially by the resiliency and the anatomical structure of the GEV 49, thus providing the valving function. The GEV 49 is similar to a flutter valve, with the gastroesophageal flap 50 being flexible and closeable against the other more stationary side.

The esophageal tract is controlled by an upper esophageal sphincter (UES) in the neck near the mouth for swallowing, and by the LES 48 and the GEV 49 at the stomach. The normal anti-reflux barrier is primarily formed by the LES 48 and the GEV 49 acting in concert to allow food and liquid to enter the stomach, and to considerably resist reflux of stomach contents into the esophagus 41 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is also referred to as the "Z-line." For the purposes of these specifications, including the claims, "stomach" means the tissue aboral of the gastroesophageal junction 52.

Figure 2:
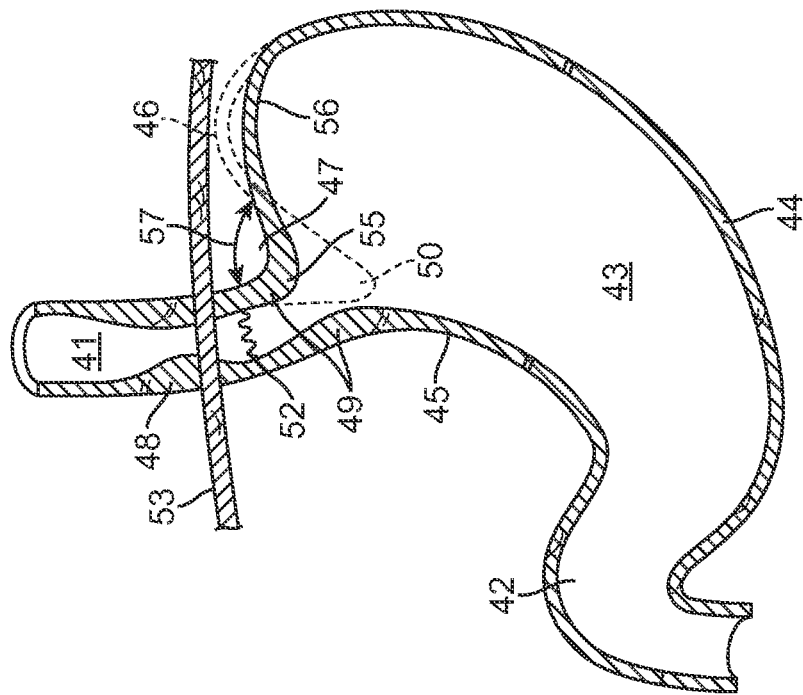
FIG. 2 is a front cross-sectional view of the esophageal-gastro-intestinal tract illustrating a Grade I normal appearance movable flap of the gastroesophageal valve (in dashed lines) and a Grade III reflux appearance of the gastroesophageal valve (in solid lines)

FIG. 2 is a front cross-sectional view of an esophageal-gastro-intestinal tract illustrating a Grade I normal appearance movable flap 50 of the GEV 49 (shown in dashed lines) and a deteriorated Grade III gastroesophageal flap 55 of the GEV 49 (shown in solid lines). As previously mentioned, a principal reason for regurgitation associated with GERD is the mechanical failure of the deteriorated (or reflux appearance) gastroesophageal flap 55 of the GEV 49 to close and seal against the higher pressure in the stomach. Due to reasons including lifestyle, a Grade I normal gastroesophageal flap 50 of the GEV 49 may deteriorate into a Grade III deteriorated gastroesophageal flap 55. The anatomical results of the deterioration include moving a portion of the esophagus 41 that includes the gastroesophageal junction 52 and LES 48 toward the mouth, straightening of the cardiac notch 47, and increasing the Angle of His 57. This effectively reshapes the anatomy aboral of the gastroesophageal junction 52 and forms a flattened fundus 56.

The deteriorated gastroesophageal flap 55 shown in FIG. 2 has a gastroesophageal valve 49 and cardiac notch 47 that are both significantly degraded. Dr. Hill and colleagues developed a grading system to describe the appearance of the GEV and the likelihood that a patient will experience chronic acid reflux. L. D. Hill, et al., *The gastroesophageal valve: in vitro and in vivo observations*, Gastrointestinal Endoscopy 1996: 44:541-547. Under Dr. Hill's grading system, the normal movable flap 50 of the GEV 49 illustrates a Grade I valve that is the least likely to experience reflux. The deteriorated gastroesophageal flap 55 of the GEV 49 illustrates a Grade III (almost Grade IV) valve. Grade III and IV valves are the most likely to experience reflux. Grades II and III reflect intermediate grades of deterioration and, as in the case of III, a high likelihood of experiencing reflux. With the deteriorated GEV represented by deteriorated gastroesophageal flap 55 and the fundus 46 moved inferior, the stomach contents are presented a funnel-like opening directing the contents into the esophagus 41 and the greatest likelihood of experiencing reflux. Disclosed subsequently are a device, assembly, and method, which may be employed to advantage according to an embodiment of the invention in restoring the normal gastroesophageal valve anatomy.

Referring now to FIG. 3, it shows a device 100 according to an embodiment of the present invention. More particularly, FIG. 3 shows those elements of the device 100 that provide for the restoration of a GEV according to this embodiment. The elements for concurrently tightening the LES according to various embodiments will be described subsequently.

The device 100 includes a longitudinal member 102 for transoral placement of the device 100 into the stomach. The device further includes a first member 104, hereinafter referred to as the chassis, and a second member 106, hereinafter referred to as the bail or mold. The chassis 104 and bail 106 are carried at the distal end of the longitudinal member 102 for placement in the stomach. The chassis 104 and bail 106 are hingedly coupled at 107 and form a tissue shaper to shape tissue of the stomach into the flap of a restored gastroesophageal valve.

The device 100 has a longitudinal passage 101 to permit an endoscope 110 to be guided through the device and into the stomach. This permits the endoscope to service as a guide for guiding the device 100 through the patient's throat, down the esophagus, and into the stomach. It also permits the gastroesophageal valve restoration procedure to be viewed at each stage of the procedure.

As described in copending application Ser. No. 11/001,666, filed Nov. 30, 2004, entitled FLEXIBLE TRANSORAL ENDOSCOPIC GASTROESOPHAGEAL VALVE RESTORATION DEVICE AND METHOD, which application is incorporated herein by reference, the device 100 is fed down the esophagus with the bail 106 substantially in line with the chassis 104. To negotiate the bend of the throat, and as described in the aforementioned referenced application, the chassis 104 and bail 106 are rendered flexible. The chassis 104 is rendered flexible by the slots 108 and the bail 106 is rendered flexible by the hingedly coupled links 112. Further details concerning the flexibility of the chassis 104 and the bail 106 may be found in the aforementioned referenced application.

To facilitate shaping of the stomach tissue, the stomach tissue is drawn in between the chassis 104 and the bail 106. Further, to enable a flap of sufficient length to be formed to function as the flap of a gastroesophageal valve, the stomach tissue is pulled down so that the fold line is substantially juxtaposed to the opening of the esophagus into the stomach. Hence, the stomach is first gripped at a point out and away from the esophagus and the grip point is pulled to almost the hinged connection 107 of the chassis 104 and bail 106. To this end, and, as further shown in FIG. 3, the device includes a tissue gripper 114. The gripper 114, in this embodiment, comprises a helical coil 115. The coil 115 is carried at the end of a cable 116 and may be attached to the end of the cable or be formed from the cable. In this embodiment, the helical coil 115 is attached to the cable 116 and is preceded by a guide 118. For a complete description of the function of the guide, together with a complete description of the manner in which a GEV may be restored with the device if FIG. 3, reference may be had to copending U.S. application Ser. No. 11/172,427, filed Jun. 29, 2005 and incorporated herein by reference in its entirety.

The helical coil 115 is shown in an approximate position to engage the stomach tissue out and away from the opening of the esophagus to the stomach. The helical coil 115 is guided into position by a guide structure 120 carried on the bail 106. The guide structure 120 comprises a guide tube 122. When the device 100 is first introduced down the esophagus into the stomach, the helical coil 115 is caused to reside well within the guide tube 122 to preclude the helical coil from accidentally or inadvertently snagging esophageal or stomach tissue.

The guide tube includes a longitudinal slit 126 having a circuitous configuration. The slit 126 permits the end of the cable to release or disassociate from the bail after the stomach tissue is gripped. The circuitous configuration of the slit 126 assures confinement of the cable 116 within the guide tube 122 until release of the cable is desired. The proximal end of the slit 126 has an enlarged portion or opening (not shown). This opening permits the cable and helical coil to reenter the lumen when the device 100 is readied for a repeated stomach tissue shaping procedure. To that end, the guide 118 has a conical surface that serves to guide the cable end back into the opening of the slit 126.

With continued reference to FIG. 3, the device 100 further comprises a fastener deployer 140. The fastener deployer includes a plurality of fastener deployment guides 142. The fastener deployment guides 142 take the form of guide lumens. Although only one guide lumen 142 is shown, it will be appreciated that the device 100 may include a plurality of such lumens without departing from the invention. The guide lumen terminates at a delivery point 144 where a fastener is driven into the molded stomach tissue. As will be seen subsequently, the fastener deployer includes at least two guides 142 so that fasteners may be deployed on opposite sides of a tissue gathering point to maintain both a restored GEV and a concurrently tightened LES.

The device 100 further includes a window 130 within the chassis 104. The window is formed of a transparent or semitransparent material. This permits gastroesophageal anatomy, and more importantly the gastroesophageal junction (Z-line) to be viewed with the endoscope 110. The window includes a location marker 132 which has a know position relative to the fastener delivery point 144. Hence, by aligning the marker with a known anatomical structure, the fastener will be delivered a known distance from or at a location having a predetermined relation to the marker. For example, by aligning the marker with the Z-line, it will be know that the fastener will be placed aboral of the Z-line and that serosa tissue will be fastened to serosa tissue. As previously mentioned, this has many attendant benefits.

It may also be mentioned at this point that the device 100 further includes an invaginator 145 including a plurality of orifices 146. These orifices 146, which alternatively may be employed on the longitudinal member 102, are used to pull a vacuum to cause the device 100 to grip the inner surface of the esophagus. This will serve to stabilize the esophagus and maintain device positioning during the procedure. This vacuum gripping of the esophagus may also be used to particular advantage if the patient suffers from a hiatal hernia. Upon being thus gripped, the esophagus may be moved downwardly with the device toward the stomach and abdominal cavity to eliminate the hiatal hernia.

Now that a device which may be used in restoring the flap of a gastroesophageal valve has been described, reference may now be made to the various embodiments herein for the concurrent tightening of an LES along with the restoration of a gastroesophageal valve. To the extent that the devices to be described herein after have elements identical to those of the device 100 of FIG. 3, like reference numerals will be employed.

In FIG. 4, a device 200 according to one embodiment of the invention is shown. Here, it may be seen that the chassis 104 and bail 106 have been brought together with a formed flap of stomach tissue 43 there between. The flap of tissue includes an inner tissue layer 180 and an outer tissue layer 182. Fasteners have not yet been deployed for maintaining the fold of stomach tissue. However, as may also be seen in the cross-sectional view of FIG. 5, fastener deployment wires or stylets 202 and 204 have been advanced down the guide lumens 142 to extend through the inner tissue layer 180 but not the outer tissue layer 182. This enables the inner tissue layer 180 to be mechanically gripped.

As may be further noted in FIGS. 4 and 5, the chassis 104 includes a longitudinal channel 210. The channel 210 provides a space for receiving the inner tissue layer 180 when it displaced into the esophageal opening and thus gathered for tightening the LES.

FIG. 6 shows the inner tissue layer 180 being gathered and displaced into the channel 210 and thus, into the esophageal opening. This is accomplished by bringing the stylets 202 and 204 together. To this end, the longitudinal member 102 is preferably formed of a compressible material. As the stylets 202 and 204 are brought towards each other, the inner tissue layer 180 is caused to fold at a gathering point 212 in between the stylets 202 and 204.

With the inner tissue layer 180 gathered as shown in FIG. 6, fasteners may now be deployed to maintain both the formed flap for the restored GEV and the gathered inner tissue layer for the tightened LES. FIGS. 7 and 8 illustrate the deployed fasteners 214 and 216. The fasteners may be deployed as described, for example, in copending U.S. application Ser. No. 10/949,737 filed Sep. 23, 2004; Ser. No. 11/172,363 filed Jun. 29, 2005; Ser. No. 11/043,903 filed Jan. 25, 2005; and Ser. No. 11/172,428 filed Jun. 29, 2005 which are hereby incorporated herein in their entireties by reference. The fasteners 214 and 216 are deployed on opposite sides of the tissue gathering point. With the fasteners 214 and 216 thus deployed, the device may be rotated and the foregoing may be repeated to form another portion of the formed flap for the restored GEV. Also, if needed, another inner tissue gathering may be carried out to provide further tightening of the LES.

Figure 9:
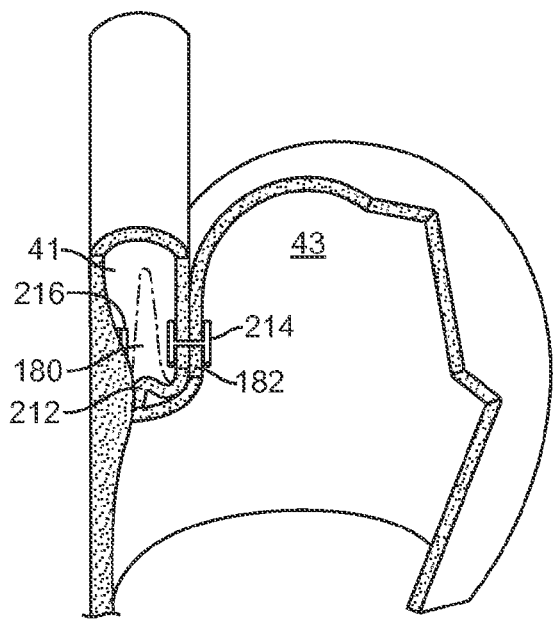
FIG. 9 is a perspective view with portions cutaway of the stomach and esophagus after the LES has been concurrently tightened according to an embodiment of the invention and the device of FIGS. 3 and 4 has been removed.
Figure 10:
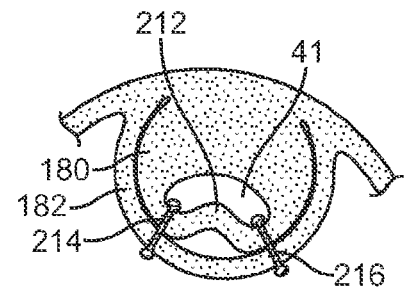
FIG. 10 is a sectional view of the anatomy illustrated in FIG. 9.

FIGS. 9 and 10 show the resulting anatomy after the GEV has been restored, the LES has been tightened, and device has been removed. Here it can be clearly seen that the gathered tissue inner layer 180 has been displaced into the esophageal opening 41 to tighten the LES and that the tissue layers 180 and 182 form a flap to in turn restore the GEV. The bottom portion of the GEV has been cut away to permit the gathered inner tissue layer tightening the LES to be clearly seen.

Figure 11:
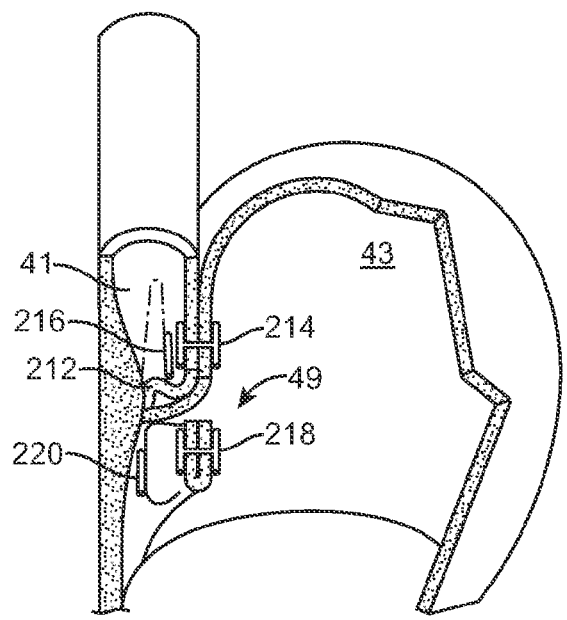
FIG. 11 is a perspective view with portions cutaway of the stomach and esophagus after the LES has been concurrently tightened according to another embodiment of the invention.

FIG. 11 illustrates that multiple levels of fasteners may be deployed. More specifically. In addition to fasteners 214 and 216, another pair of fasteners 218 and 220 have also been deployed on opposite sides of the tissue gathering point. Also, FIG. 11 shows the entire extent of the restored GEV 49 although a middle portion has been cut away to permit all of the features of the resulting anatomy to be visible.

Figure 12:
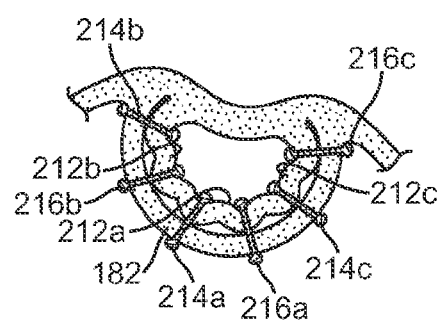
FIG. 12 is a sectional view of the anatomy illustrated in FIG. 11.

FIG. 12 shows a tightened LES after the inner tissue layer is gathered for each of three incremental rotations of the device 200. Three separate tissue gathering points 212a, 212b, and 212c are created and maintained by fasteners 214a and 216a, 214b and 216b, and 214c and 216c, respectively. This creates a pleated tissue structure as shown.

Figure 13:
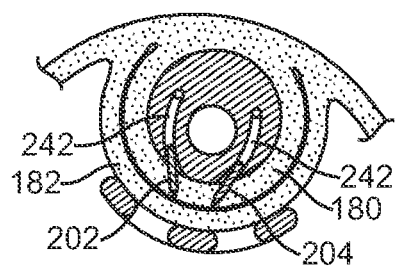
FIGS. 13 through 16 are sectional views illustrating incremental steps in concurrently tightening the LES according to a further embodiment of the invention.

FIGS. 13 through 16 illustrate another embodiment of the present invention. Here, the fastener guide lumens 242 cause the gathering of the inner tissue layer 180. More specifically, the lumens 242 are arranged to define converging trajectories of the fastener deployment stylets 202 and 204. FIG. 13 more specifically shows the converging stylets 202 and 204 projecting through the tissue layers 180 and 182.

Figure 14:
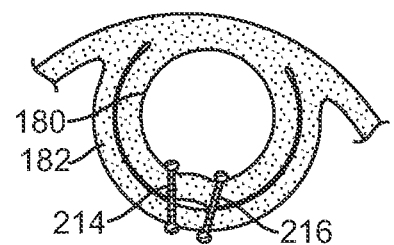
Figure 15:
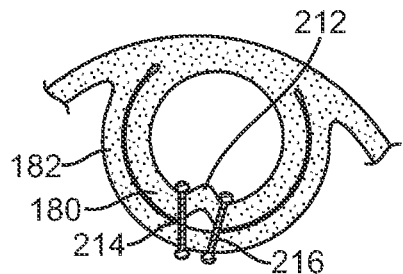
Figure 16:
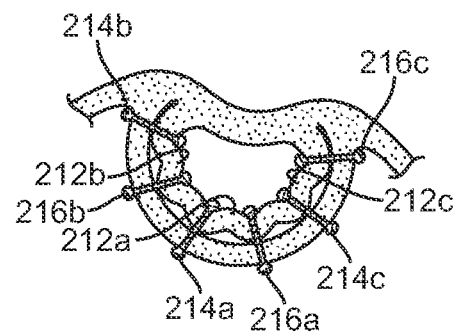
Figure 17:
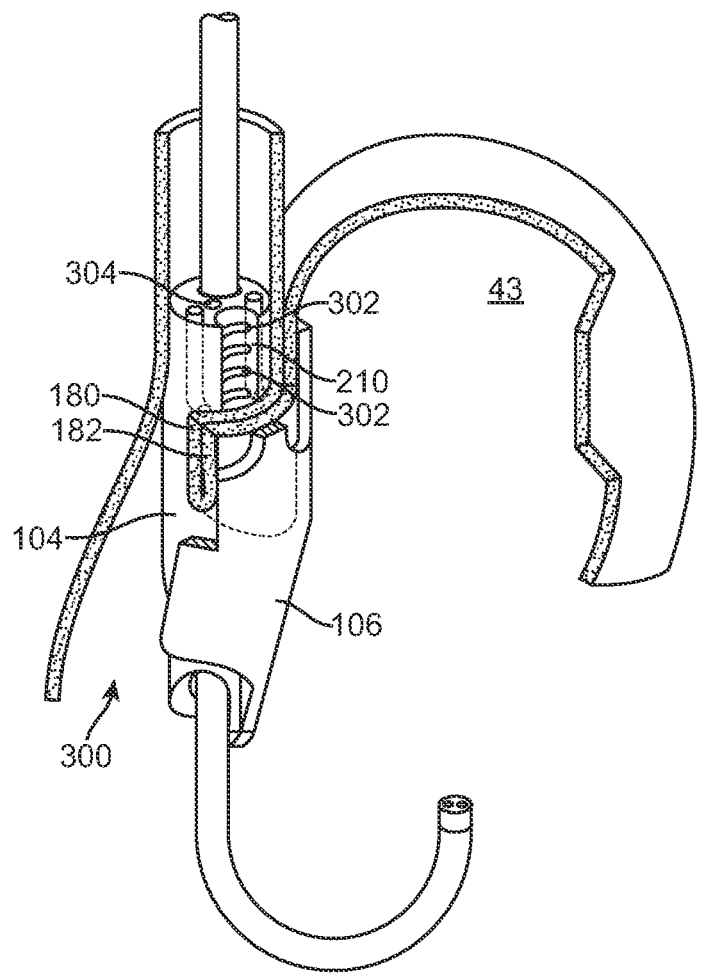
FIG. 17 is another perspective view with portions cutaway illustrating alternative internal elements of the device of FIG. 3 at an initial stage of concurrent tightening of the LES according to a still further embodiment of the invention.

FIG. 14 shows the tissue layers 180 and 182 together with the fasteners 214 and 216 just after the fasteners are deployed with the converging stylets. As soon as the fasteners 214 and 216 are deployed, the tissue layers 180 and 182 shift to establish equilibrium. The result may be seen in FIG. 15. The shifting of the tissue layers 180 and 182 has caused the inner tissue layer to gather at a gathering point 212. Having been secured by the fasteners 214 and 216, the gathered tissue will tighten the LES. At the same time, while the fasteners are deployed, a flap of a GEV restored as previously described is also secured. If this is repeated for each incremental rotation of the device, the pleated structure of gathering points 212a, 212b, and 212c are created and maintained by fasteners 214a and 216a, 214b and 216b, and 214c and 216c, respectively.

Figure 18:
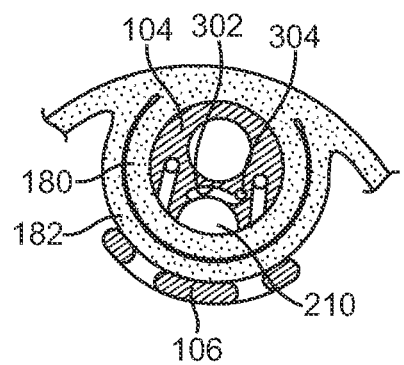
FIG. 18 is a sectional view illustrating a manner in which the device of FIG. 17 may first grip fundus tissue for concurrently tightening the LES.

In FIGS. 17 through 21, another embodiment is shown wherein the tissue, gathered for tightening the LES, is gathered by vacuum displacement. More specifically, FIG. 17 and the sectional view of FIG. 18 show another device 300 for restoring a GEV and tightening the LES wherein a flap of stomach tissue for restoring the GEV is formed between the chassis 104 and the bail 106 of the device 300. The chassis 104 includes the longitudinal channel 210 for receiving the gathered tissue. Here, however, the device further includes vacuum ports 302 that communicate with the channel 210. The ports 302 communicate with a lumen 304 that extends from the chassis 104 and through the longitudinal member for coupling to a vacuum source. The resulting vacuum pull through the ports 304 will cause the tissue of the inner tissue layer 180 to be displaced and gathered into the channel 210.

Figure 19:
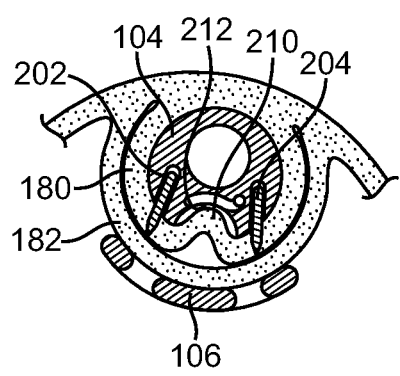
FIG. 19 is a sectional view illustrating a manner in which the device of FIG. 17 grips fundus tissue for concurrently tightening the LES and deploying fasteners to maintain a tightened LES.

The sectional view of FIG. 19 illustrates the inner tissue layer 180 being displaced by the vacuum pull into the channel 210 at a gathering point 212. Also, the fastener deployment stylets 202 and 204 have been advanced through the inner tissue layer 180. In this state, the assemblage is now ready for the deployment of fasteners 214 and 216 to maintain the restored GEV and the tightened LES.

Figure 20:
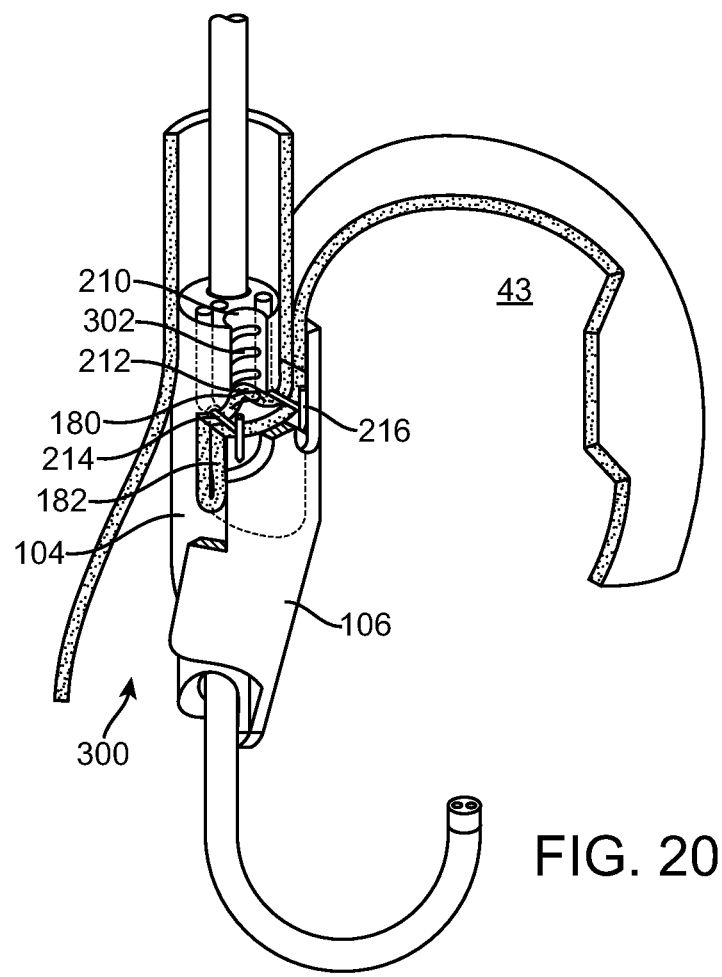
FIG. 20 is another perspective view with portions cutaway illustrating the alternative internal elements of the device of FIG. 3 after concurrent tightening of the LES and deployment of fasteners.
Figure 21:
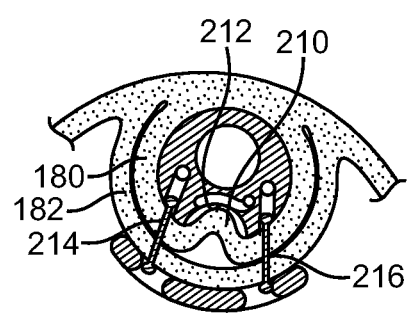
FIG. 21 is another sectional view illustrating the tightened and fastened LES resulting from use of the device of FIGS. 17 and 20.

FIGS. 20 and 21 show the fasteners 214 and 216 after deployment. Again, the fasteners are deployed on opposite sides of the gathering point 212. Of course, as previously shown and described with reference to FIG. 11, additional fasteners may also be deployed. Still further, if additional flap portions are to be formed for restoring the GEV, the device may be rotated and the tissue shaping procedure may be repeated. The inner tissue layer 180 may receive additional gathering as well if further LES tightening is necessary.

Hence, as may be seen from the foregoing, according to various embodiments shown and described herein, the present invention provides an assembly and method for restoring a GEV and concurrently therewith, tightening the LES. The GEV restoration and LES tightening may both be performed transorally in a minimally invasive manner. Since both therapies are concurrently provided in the same procedure, the patient is spared the inconvenience of and recovery from separate procedures.

While particular embodiments of the present invention have been shown and described, modifications may be made, and it is thereto intended in the appended claims to cover all such changes and modifications which fall within the true spirit and scope of the invention.

What is claimed is:

1. A method of treating a stomach disorder involving a patient's stomach, esophagus, and esophageal opening into the stomach, comprising:
    forming a gastroesophageal valve from fundus tissue using a device having a longitudinal member, the gastroesophageal valve having an inner tissue layer and an outer tissue layer, the inner tissue layer being positioned between the longitudinal member and the outer tissue layer;
    gathering the inner tissue layer of the fundus tissue to reduce the esophageal opening by displacing the inner tissue layer into an esophageal opening to create a fundus fold, the fundus tissue being gripped at two spaced apart positions of the inner tissue layer of the gastroesophageal valve, wherein a gathering step includes a step of moving the two spaced apart positions of the inner tissue layer of the gastroesophageal flap valve towards each other to form the fundus fold;
    the gathering step is carried out with the device having a first stylet and a second stylet, the first and second stylets extending into the inner tissue layer and not the outer tissue layer at the spaced apart positions, the first and second stylets being brought toward one another to gather the fundus tissue of the inner tissue layer; and
    deploying at least one fastener to maintain both the formed gastroesophageal valve and the fundus fold.

2. The method of claim 1, wherein the gathering step comprises mechanically gripping the fundus tissue.

3. The method of claim 1, wherein the gathering step includes gathering the fundus tissue at a gathering point and wherein a deploying step comprises deploying a fastener on opposite sides of the gathering point.

4. The method of claim 1, wherein a deploying step comprises deploying at least a pair of fasteners spaced apart and wherein the gathering step comprises providing the fasteners with converging trajectories during deployment.

5. The method of claim 1, wherein the device is advanced into the stomach, and wherein the step of forming the gastroesophageal valve comprises folding the fundus tissue with the device so that serosa tissue contacts serosa tissue to form the gastroesophageal valve.

6. The method of claim 1, wherein the gathering step comprises mechanically gripping the inner tissue layer.

7. The method of claim 1, wherein the gathering step includes gathering the inner tissue layer at a gathering point and wherein a deploying step comprises deploying a fastener with the device through the inner and outer tissue layers on opposite sides of the gathering point.

8. The method of claim 1, wherein a deploying step comprises driving at least a pair of fasteners spaced apart and from the inner tissue layer to and through the outer tissue layer and wherein the gathering step comprises providing the fasteners with converging trajectories while being driven.

* * * * *